United States Patent [19]
Henderson et al.

[11] Patent Number: 6,149,591
[45] Date of Patent: Nov. 21, 2000

[54] REFRACTOMETRIC DEVICES ESPECIALLY ADAPTED FOR THE IN VIVO DETECTION OF REFRACTIVE INDICES OF CERVICAL MUCUS

[75] Inventors: Marcus H. Henderson; David F. Katz, both of Durham, N.C.

[73] Assignee: Duke University, Durham, N.C.

[21] Appl. No.: 09/204,163

[22] Filed: Dec. 3, 1998

Related U.S. Application Data

[63] Continuation-in-part of application No. 08/804,057, Feb. 21, 1997, abandoned.

[51] Int. Cl.[7] ................................................... G01N 21/41
[52] U.S. Cl. ......................... 600/407; 600/476; 600/551; 356/133
[58] Field of Search .................................... 600/407, 476, 600/551; 356/128–133

[56] References Cited

U.S. PATENT DOCUMENTS

| | | | |
|---|---|---|---|
| H1470 | 8/1995 | Ewing et al. ........................... 356/128 |
| 1,480,391 | 1/1924 | Hausser . |
| 1,940,373 | 12/1933 | Schoenberg . |
| 2,062,588 | 12/1936 | Logan et al. . |
| 2,597,425 | 5/1952 | Aiken et al. . |
| 3,628,867 | 12/1971 | Brady ..................................... 356/136 |
| 3,891,325 | 6/1975 | Schuster et al. . |
| 3,926,037 | 12/1975 | Kopito et al. ........................... 600/551 |
| 3,975,097 | 8/1976 | Minto ..................................... 356/128 |
| 4,019,820 | 4/1977 | Kopito et al. . |
| 4,306,805 | 12/1981 | Arrington .............................. 356/133 |
| 4,498,481 | 2/1985 | Lemke . |
| 4,534,362 | 8/1985 | Schmumacher et al. ............... 600/551 |
| 4,564,292 | 1/1986 | Omet ..................................... 356/133 |
| 4,685,471 | 8/1987 | Regas et al. ............................ 600/551 |
| 4,691,714 | 9/1987 | Wong et al. ............................ 600/551 |
| 4,699,511 | 10/1987 | Seaver .................................... 356/136 |
| 4,704,029 | 11/1987 | Van Heuvelen ........................ 356/136 |
| 4,753,247 | 6/1988 | Krisner .................................. 600/551 |
| 4,806,013 | 2/1989 | Bodenheimer et al. ................ 356/133 |
| 4,834,533 | 5/1989 | Horike et al. .......................... 356/133 |
| 4,997,278 | 3/1991 | Finlan et al. ........................... 356/128 |
| 4,998,022 | 3/1991 | Tregay ................................... 356/136 |
| 5,026,139 | 6/1991 | Klainer et al. ......................... 356/133 |
| 5,055,699 | 10/1991 | Konig et al. ........................... 356/133 |
| 5,059,396 | 10/1991 | Opitz et al. . |
| 5,094,517 | 3/1992 | Franke . |
| 5,165,005 | 11/1992 | Klainer et al. ......................... 356/128 |
| 5,173,747 | 12/1992 | Boiarski et al. ....................... 356/128 |

(List continued on next page.)

*Primary Examiner*—Ruth S. Smith
*Attorney, Agent, or Firm*—Nixon & Vanderhye P.C.

[57] ABSTRACT

Devices for detecting hydration of cervical mucus (which is indicative of the course of a female's reproductive cycle) include a detector having a light source, a photoreceptor and a light guide positioned so as to guide light from the light source to the photoreceptor. The light guide includes at least one active surface to be wetted by the cervical mucus. The detector may be planar or curvelinear and may be embedded within a distal sensing head or extend upright therefrom (e.g., so as to somewhat penetrate the external cervical os during use). Most preferably, the light guide is fabricated from a fluorocarbon polymer. For use in vivo, the device will preferably include a proximal handle which allows the user to manipulate the distal sensing head into close proximity to the external cervical os. The handle may include a source of electrical power (e.g., a DC battery pack, solar cell or the like), a processor for processing the signal received from the photoreceptor indicative of the cervical mucus refractive index, and a human-readable display (e.g., an alpha-numeric display, light indicator, analog display or the like). A relatively slender (as compared to the handle) stem operatively connects the handle to the distal sensing head. The sensing head may be formed as a one-piece structure with the stem and angled relative thereto so as to assist in placement of the detector in close proximity to the external cervical os. Alternatively, the sensing head may be connected to the stem to allow for relative pivotal articulation to permit selective adjustment of the sensing head's angular orientation relative to the stem. The stem itself may be entirely rigid, or may be flexible (e.g., longitudinally flexible, but torsionally rigid).

36 Claims, 13 Drawing Sheets

U.S. PATENT DOCUMENTS

| | | |
|---|---|---|
| 5,191,206 | 3/1993 | Boiarski et al. . |
| 5,209,238 | 5/1993 | Sundhar .................................. 600/551 |
| 5,210,404 | 5/1993 | Cush et al. ............................... 356/128 |
| 5,240,010 | 8/1993 | Weinmann ............................. 600/551 |
| 5,351,692 | 10/1994 | Dow et al. . |
| 5,391,891 | 2/1995 | Wiegleb et al. . |
| 5,396,325 | 3/1995 | Carome et al. ......................... 356/128 |
| 5,422,495 | 6/1995 | Cohn . |
| 5,439,647 | 8/1995 | Saini . |
| 5,452,076 | 9/1995 | Schopper et al. ....................... 356/128 |
| 5,477,318 | 12/1995 | Ohsaki et al. .......................... 356/136 |
| 5,483,346 | 1/1996 | Butzer . |
| 5,499,631 | 3/1996 | Weiland .................................. 600/547 |
| 5,565,978 | 10/1996 | Okubo et al. ........................... 356/128 |
| 5,572,315 | 11/1996 | Krell ....................................... 356/136 |

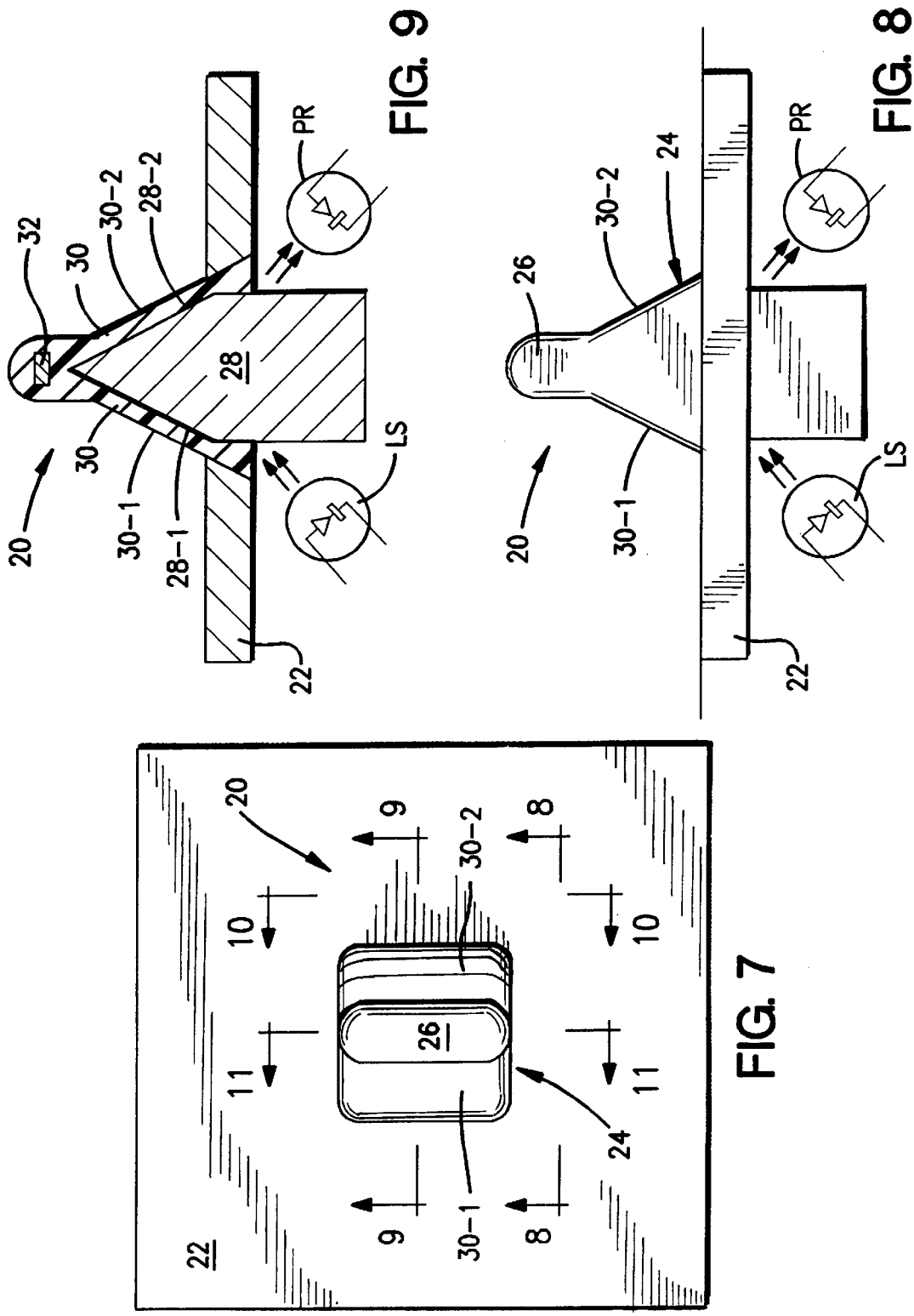

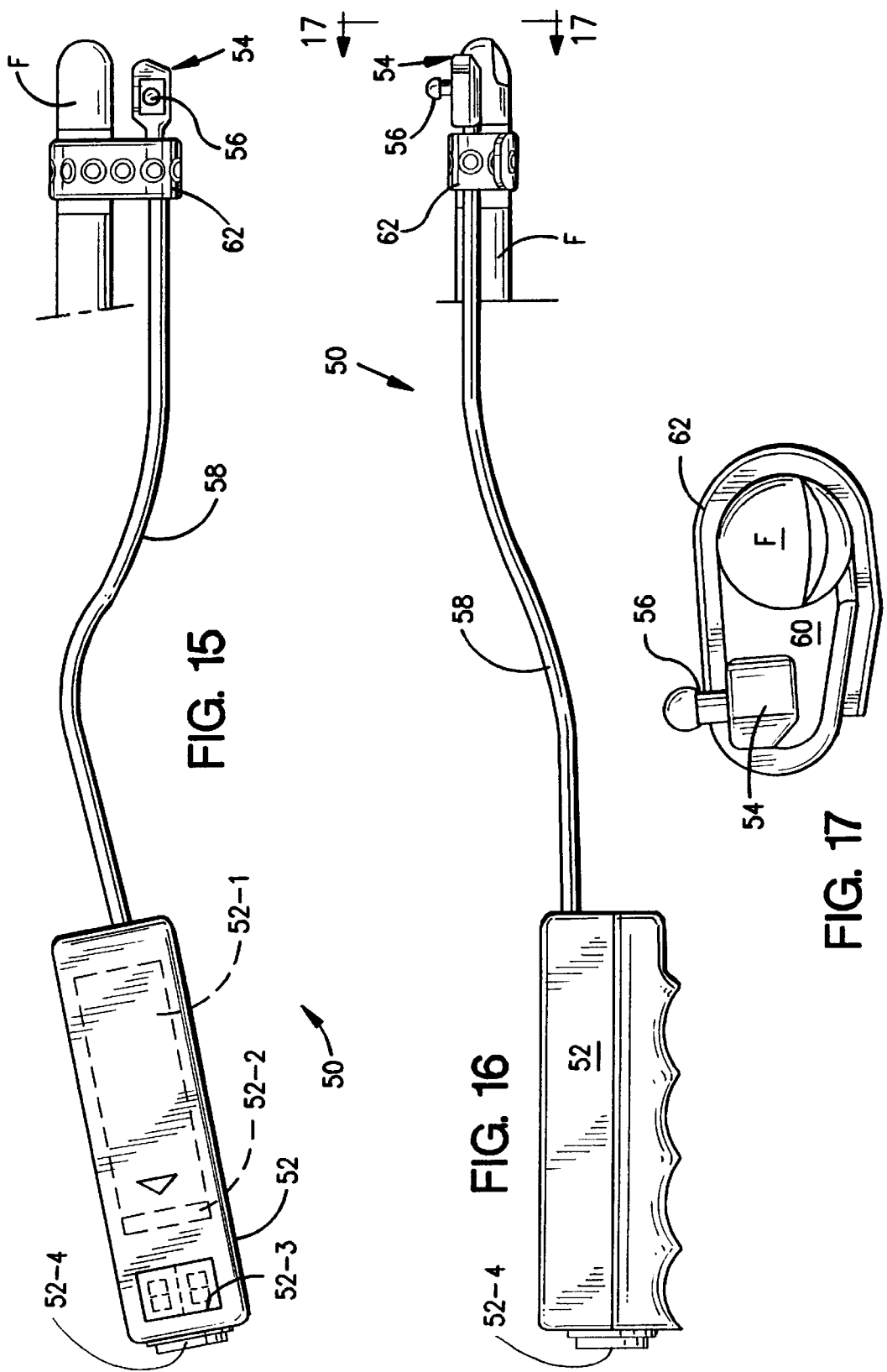

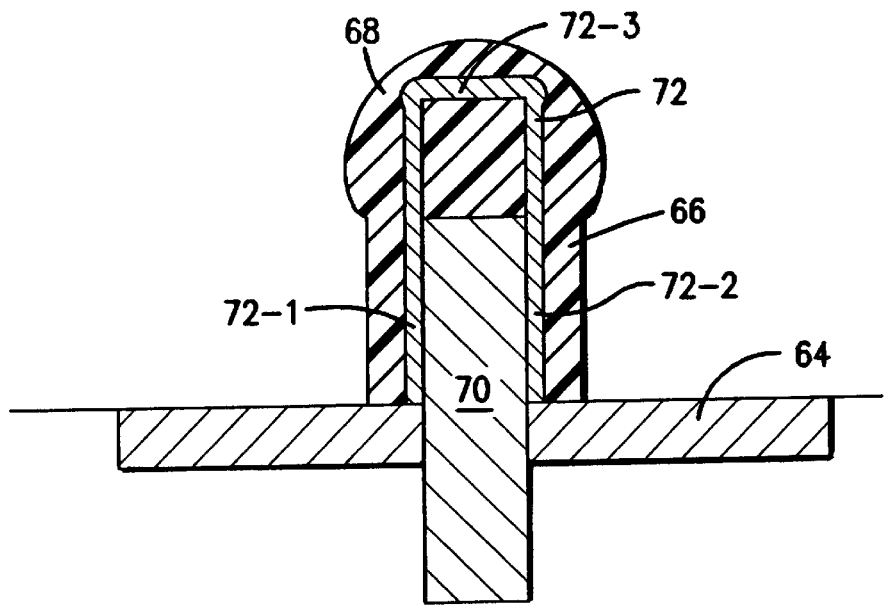
FIG. 20
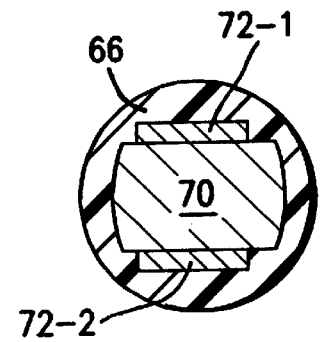
FIG. 21       FIG. 22
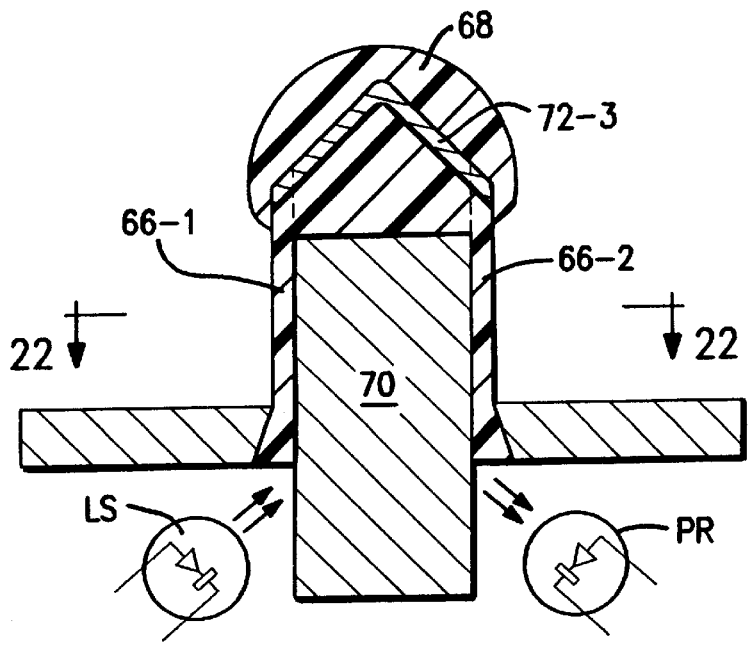

REFRACTOMETRIC DEVICES ESPECIALLY ADAPTED FOR THE IN VIVO DETECTION OF REFRACTIVE INDICES OF CERVICAL MUCUS

CROSS-REFERENCE TO PARENT APPLICATION

This application is a continuation-in-part of now abandoned application Ser. No. 08/804,057 filed on Feb. 21, 1997, the entire content of which is expressly incorporated hereinto by reference.

GOVERNMENT RIGHTS STATEMENT

This invention was made with Government support under Grant No. DPE-3061-A-00-1029-00 awarded by the U.S. Agency of International Development (US AID). The Government has certain rights in the invention.

FIELD OF INVENTION

The present invention relates generally to refractometric devices. More particularly, the present invention relates to the field of refractometric devices which allow in vivo ovulation detection in female mammals.

BACKGROUND AND SUMMARY OF THE INVENTION

Detecting with reasonable precision the fertile period of the female reproductive cycle would have significant benefits from a human "family planning" aspect as well as with animal husbandry. For example, by detecting the fertile period, a woman would be able to determine when intercourse would likely lead to conception. Such information could therefore be used by the woman to either refrain from or engage in intercourse if contraception or conception is desired, respectively. Similarly, livestock breeders would be able to maximize successful inseminations with knowledge of the ovulation cycle of the particular breeding animal.

It is well known that a number of physiological changes ensue during a woman's menstrual cycle and various tests have been developed as an aid to family planning. For example, it is known that the water content of vaginal mucus varies during the menstrual cycle. In this regard, U.S. Pat. No. 4,019,820 to Kopito et al (the entire content of which is incorporated expressly hereinto by reference) discloses an in vitro device which detects ovulation during a menstrual cycle using the transmissivity and/or diffusivity properties of vaginal mucus. That is, according to Kopito et al '820, a vaginal mucus sample must first be positioned between a pair of plates at a specific pressure and temperature in order to provide a mucus stratum of predetermined thickness. A photometer then measures the optical transmissivity and/or diffusivity in order to determine the phase of the menstrual cycle.

The techniques disclosed by Kopito et al '820 are not without problems. Specifically, since the apparatus is quite cumbersome and the mucus sample must be positioned with great care and accuracy with respect to the photometer, it is impractical for "home" use, but instead must be administered by clinical technicians. Furthermore, since the device is only capable of detecting vaginal mucus properties in vitro, there is a real risk that the water content in the mucus will change in the short time it takes to obtain a sample and to prepare it for testing in the Kopito et al '820 apparatus, thereby potentially leading to inaccurate readings.

What has been needed in this art, therefore, is a relatively simply device that can be employed in vivo to detect the ovulation period of females. It is towards fulfilling such a need that the present invention is directed.

Broadly, the present invention relates to a device that detects in vivo physiological changes in a female's cervical mucus. These changes correlate with the timing of ovulation and thus provide a marker for the fertile period of the menstrual cycle. The fertile period is the time interval during which unprotected intercourse can lead to pregnancy. The period extends several days before the day of ovulation and ends immediately after that day. More particularly, the device of the present invention measures the water content, or hydration of cervical mucus, which has been shown to increase several days before ovulation. These changes in mucus hydration correlate with the pre-ovulation rise in luteinizing hormone (LH) which only precedes ovulation by 24–36 hours, and thus occurs after the onset of the fertile period. Other hormone changes, e.g., those of estradiol or progesterone, are less consistent within and among women than the increase in mucus hydration and thus are less robust markers of the fertile period. The device of this invention therefore measures in vivo the mucus hydration by its direct correlate, the index of refraction of the mucus. As a result, problems associated with in vitro measurement of mucus hydration (e.g., possible mucus dehydration when a sample is removed from the body) are eliminated.

The device of this invention generally includes a refractive index detector having a light source, a photoreceptor and a light guide positioned so as to guide light from the light source to the photoreceptor. The light guide includes at least one active surface to be wetted by the cervical mucus. The detector may be planar or curvelinear and may be embedded within a distal sensing head or extend upright therefrom (e.g., so as to somewhat penetrate the external cervical os during use). Most preferably, the light guide is fabricated from a fluorocarbon polymer.

Most preferably, the device of this invention will include a proximal handle which allows the user to manipulate the distal sensing head into close proximity to the external cervical os. The handle may include a source of electrical power (e.g., a DC battery pack, solar cell or the like), a processor for processing the signal received from the photodetector indicative of the cervical mucus refractive index, and a human-readable display (e.g., an alpha-numeric display, light indicator, analog display or the like). A relatively slender (as compared to the handle) stem operatively connects the handle to the distal sensing head. The sensing head may be formed as a one-piece structure with the stem and angled relative thereto so as to assist in placement of the detector in close proximity to the external cervical os. Alternatively, the sensing head may be connected to the stem to allow for relative pivotal articulation to permit selective adjustment of the sensing head's angular orientation relative to the stem. The stem itself may be entirely rigid, or may be flexible.

Further aspects and advantages of this invention will become more clear after careful consideration is given to the detailed description of the preferred exemplary embodiments thereof which follow.

BRIEF DESCRIPTION OF THE DRAWINGS

Reference will hereinafter be made to the accompanying drawings wherein like reference numerals throughout the various FIGURES denote like structural elements, and wherein;

FIG. 7 is a plan view of the detector depicted in FIG. 6;

FIG. 8 is an end elevational view of the detector depicted in FIG. 7 as taken along line 8—8 therein;

FIG. 9 is a latitudinal cross-sectional view of the detector depicted in FIG. 7 as taken along line 9—9 therein;

FIG. 15 is a top plan view of another embodiment of a refractometric device in accordance with the present invention;

FIG. 16 is side elevational view of the device depicted in FIG. 15;

FIG. 17 is an enlarged end elevational view of the device depicted in FIG. 15 as taken along line 17—17 in FIG. 16;

FIGS. 20 and 21 are each cross-sectional elevational views of the detector depicted in FIG. 18 as taken along lines 20–20 and 21—21, respectively, therein;

FIG. 22 is a cross-sectional plan view of the detector depicted in FIG. 18 as taken along line 22—22 in FIG. 21.

DETAILED DESCRIPTION OF THE PREFERRED EXEMPLARY EMBODIMENTS

Figure 1:
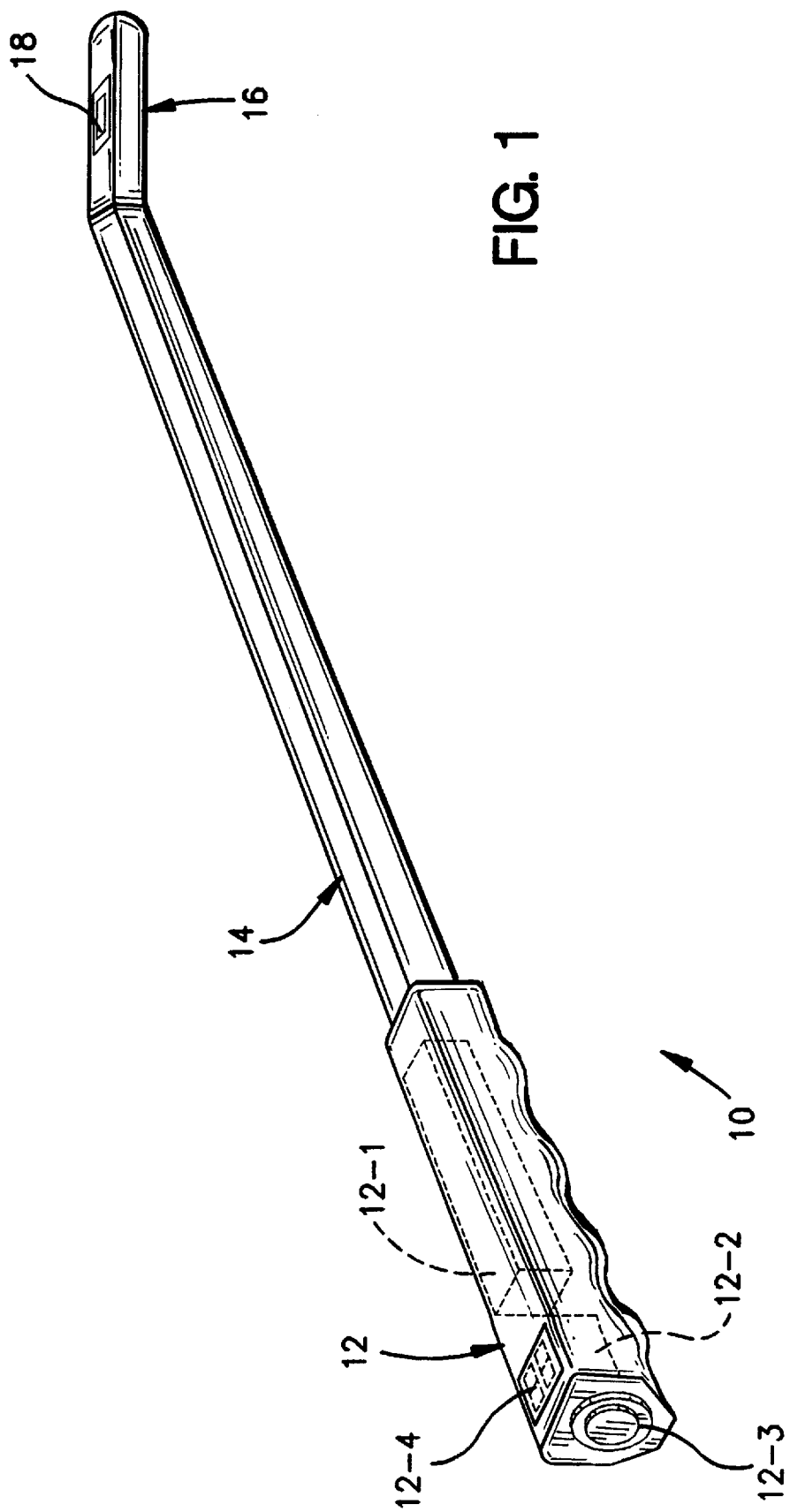
FIG. 1 is a perspective view of one embodiment of a refractometric device in accordance with the present invention.

A particularly preferred embodiment of a device 10 in accordance with the present invention is depicted in FIG. 1. As shown, the device 10 generally includes a proximal handle 12 to allow the device 10 to be gripped and manually manipulated during use, and a relatively slender (as compared to the handle) stem 14 extending distally from the handle 12 along a common axis. The stem 14 terminates in a distal sensing head 16 which is angularly oriented with respect to the stem 14 (e.g., 30°± which, for many women, approximates the angle between their vagina and external cervical os). Most preferably, the stem 14 and distal sensing head 16 are formed as a one piece structure from a biomedically compatible plastics material.

The distal sensing head 16 carries a refractive index detector 18 for placement against the woman's external cervical os during use. As will be explained in greater detail below, the detector 18 measures the refractive index of the woman's cervical mucus which, in turn, is indicative of ovulation. The detector 18 is connected electrically to an electrical power source 12-1 (e.g., a battery pack, photocells or the like) and processor 12-2 contained within the handle 12 via wires (not shown) embedded in the stem 14. A button 12-3 at the proximal end of the handle 12 activates the detector 18 and causes a signal indicative of the refractive index to be supplied to the processor 12-2. The processor 12-2 may then display the signal in a human-readable format via a visual display panel 12-4. In this regard, the display panel 12-4 may numerically display the detected refractive index of the cervical mucus and/or may process the signal to display a light signal indicative of a fertile period should the refractive index deviate from a predetermined value.

Figure 2:
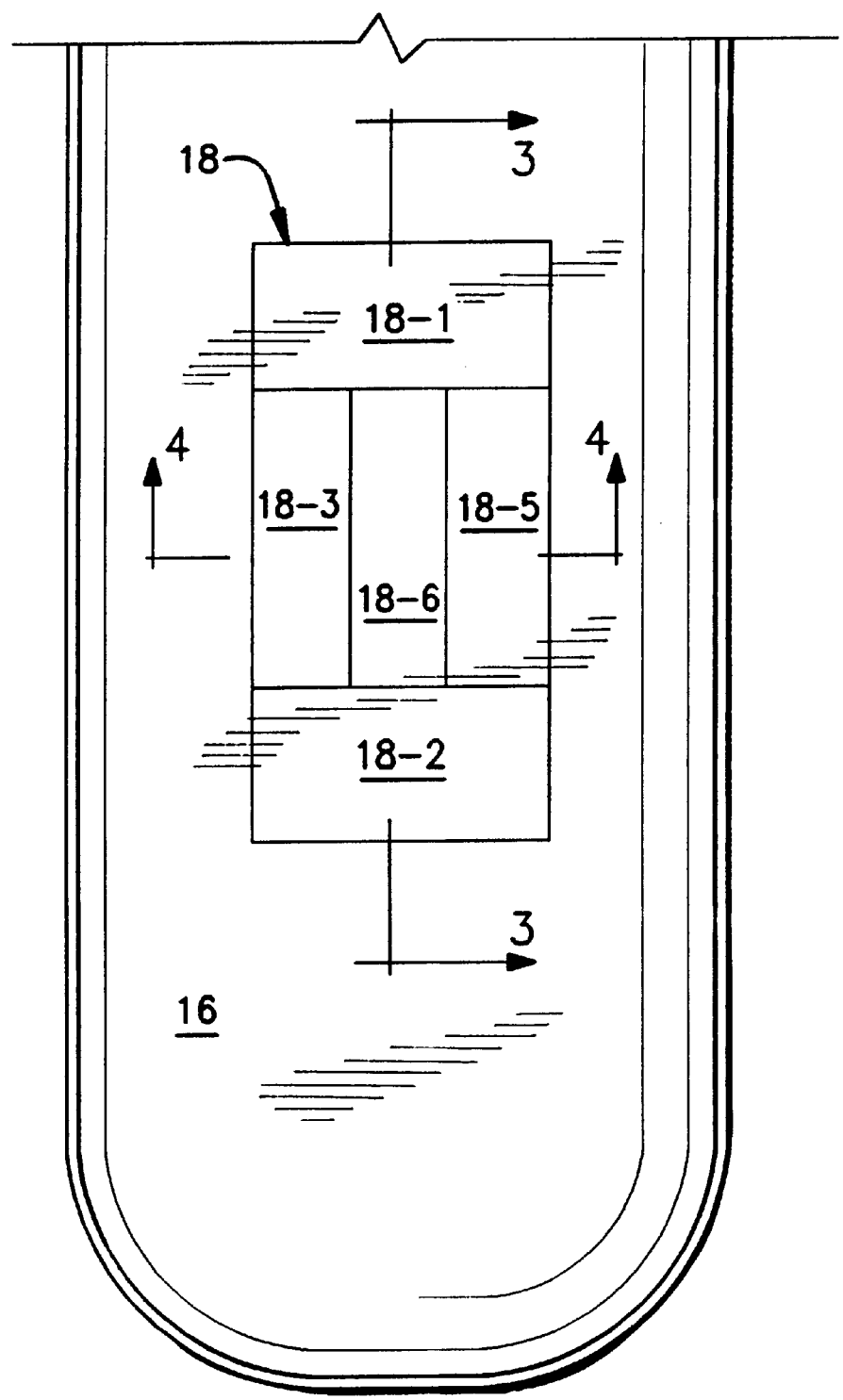
FIG. 2 is an enlarged top plan view of the distal (detector) end of the device shown in FIG. 1.
Figure 3:
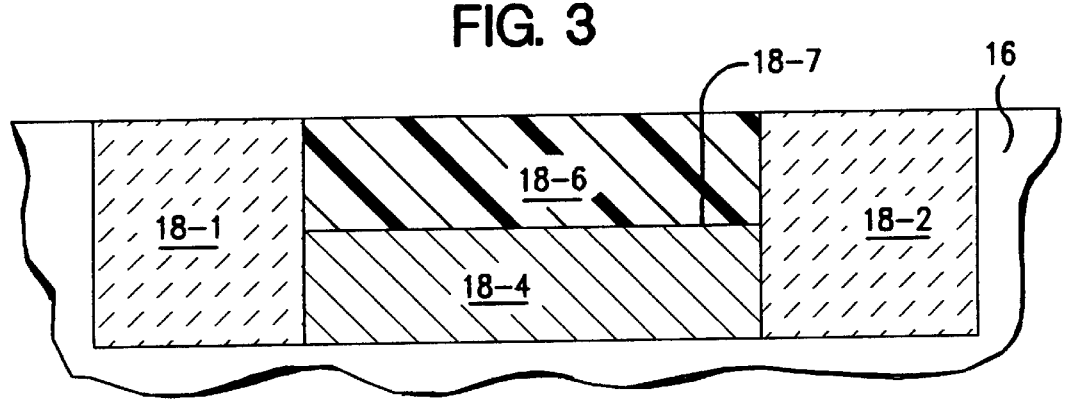
FIG. 3 is a longitudinal cross-sectional elevational view through the detector employed in the device of this invention as taken along lines 3—3 in FIG. 2.
Figure 4:
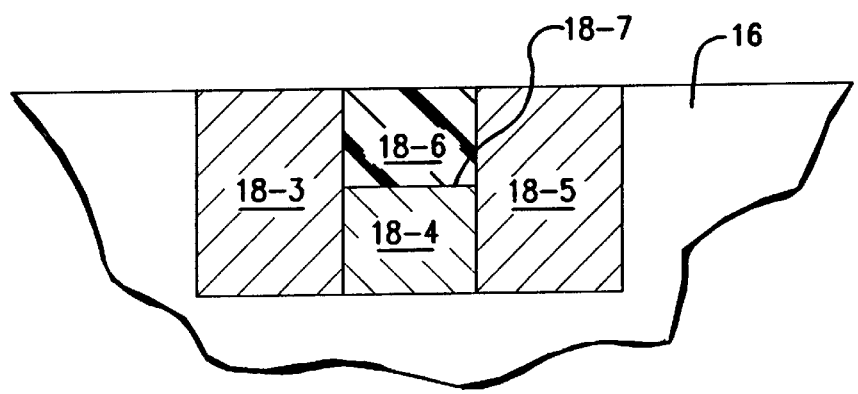
FIG. 4 is a latitudinal cross-sectional elevational view through the detector employed in the device of this invention as taken along lines 4—4 in FIG. 2.

Accompanying FIGS. 2–4 show in greater detail the refractive index detector 18 that is employed in the device 10 described above with reference to FIG. 1. In this regard, the detector 18 includes a light source 18-1 (e.g., a conventional LED) and a photodetector 18-2 (e.g., a conventional photodiode) axially spaced from the light source 18-1. An elongated channel having a U-shaped cross-section is formed axially between the light source 18-1 and photodetector 18-2 by means of stainless steel support rods 18-3, 18-4 and 18-5. The channel is filled with a fluorocarbon polymer (e.g., Teflon® FEP fluorocarbon polymer commercially available from DuPont) which serves as the light guide 18-6 for the detector 18. The surface 18-7 of the support rod 18-4 in contact with the fluorocarbon light guide 18-6 is polished so as to provide a light-reflective surface interface therebetween.

As shown in FIGS. 2 and 3, the upper surfaces of the light source, 18-1, photodetector 18-2, support rods 18-3 and 18-5 and the light guide 18-6 are each substantially co-planar with the upper surface of the sensing head 16 so as to present a smooth external surface to the user. In addition, although not shown in the drawings, the upper surfaces of the light source, 18-1, photodetector 18-2 and support rods 18-3 and 18-5 may be covered by an opaque film coating (e.g., black paint) so as to mask all available light paths except for that provided by the light guide 18-6.

Virtually any fluorocarbon polymer having a refractive index (ASTM D-542) of between about 1.335 to about 1.450, and more preferably between about 1.341 to about 1.347 may be used in the practice of this invention. The fluorocarbon polymer employed in this invention will also exhibit, or may be processed to exhibit, an optical clarity of about 98% or greater, and more preferably about 99% or greater. As used herein and in the accompanying claim, the term "optical clarity" is 100% minus the percent haze value as determined by ASTM D 1003-61 (reapproved 1988, incorporated fully by reference herein).

The term "fluorocarbon polymer" as used herein and in the accompanying claims is meant to refer to any polymer, copolymer, terpolymer and the like having at least one (preferably more than one) fluorocarbon moiety in a repeat unit of its molecular chain. By way of example, preferred fluorocarbon polymers that may be employed in accordance with the present invention include copolymers comprised of tetrafluoroethylene with hexafluoropropylene comonomers, polychlorotrifluoroethylene, ethylene-tetrafluoroethylene copolymers, polyvinylidene fluoride polymers, and polyvinyl fluoride polymers. Particularly preferred according to this invention are copolymers comprised of tetrafluoroethylene with hexafluoropropylene comonomers commercially available from DuPont under the registered trademark Teflon® FEP fluorocarbon polymers. The preferred fluorocarbon polymers will exhibit a refractive index (ASTM D-542) of between about 1.341 to about 1.347. The optical clarity of the preferred fluorocarbon polymers may be increased by heating the polymer to greater than its glass transition temperature ($T_g$) followed by rapid quenching of the heat-treated polymer. The resulting heat-treated and quenched fluorocarbon polymer will most preferably exhibit an optical clarity of about 98% or greater, and more preferably about 99% or greater.

Figure 5:
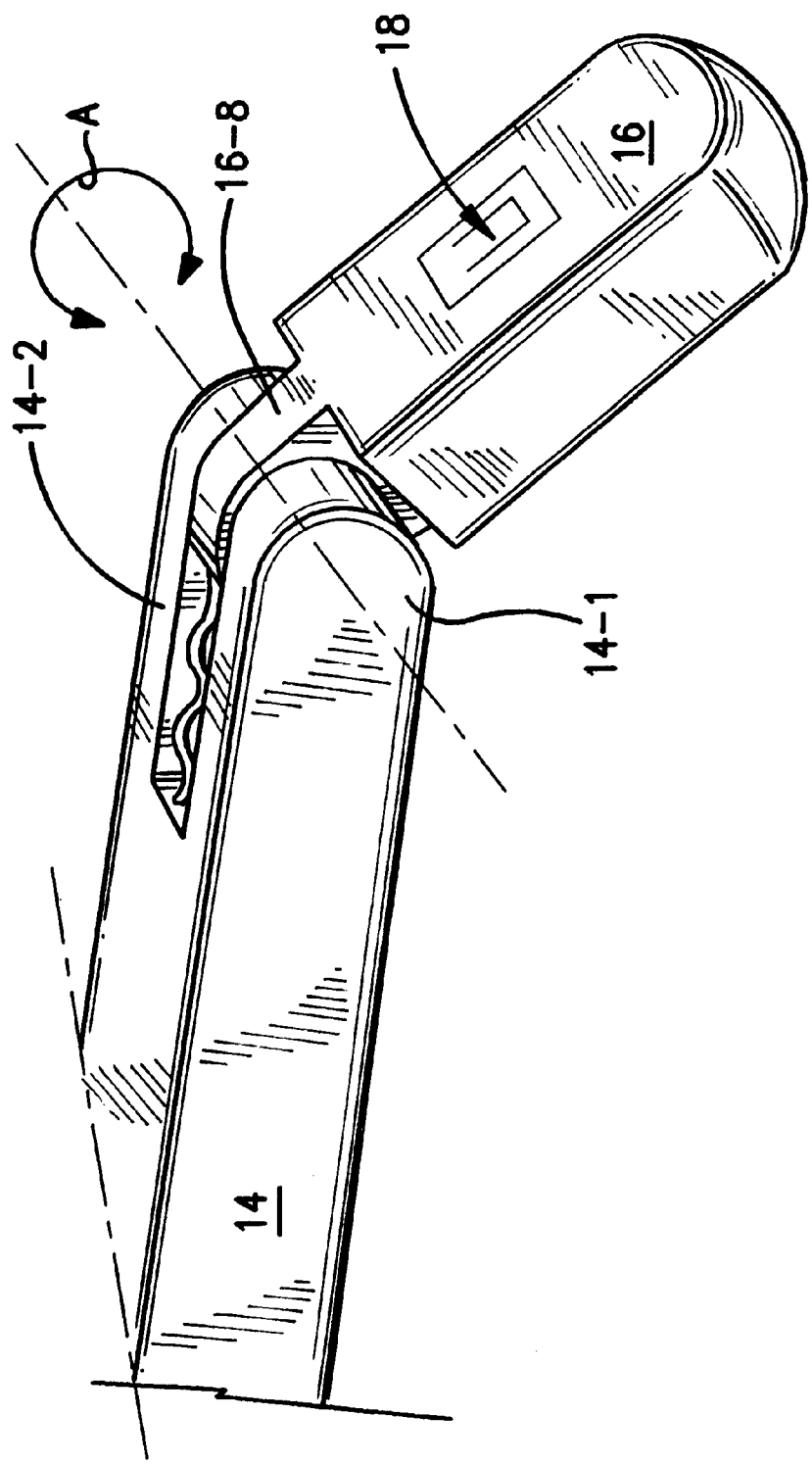
FIG. 5 is an enlarged perspective view showing a modified distal (sensing) end in accordance with another embodiment of this invention.
Figure 6:
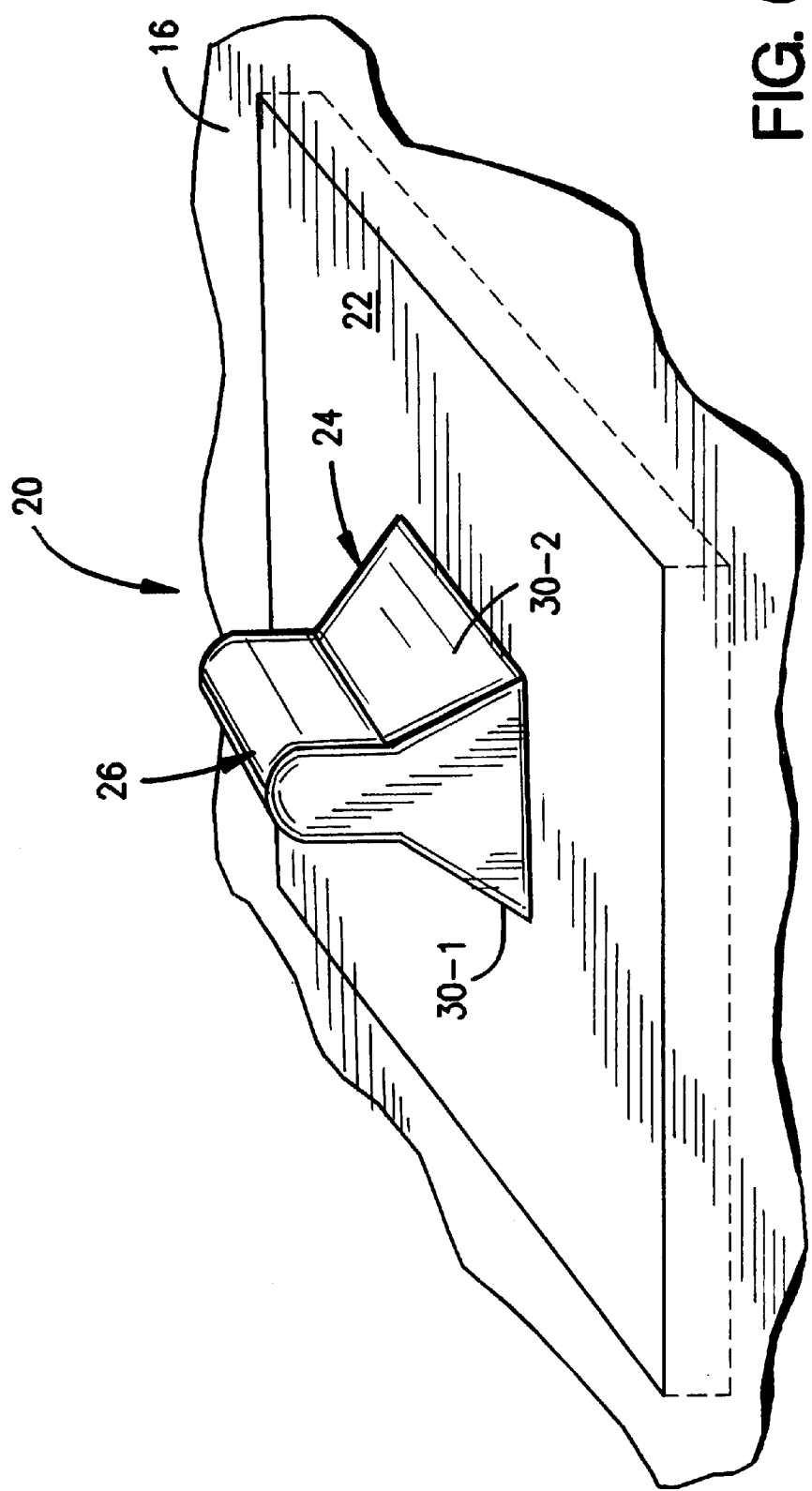
FIG. 6 is an enlarged perspective view showing a differently configured detector that may be employed in the devices of this invention.
Figure 10:
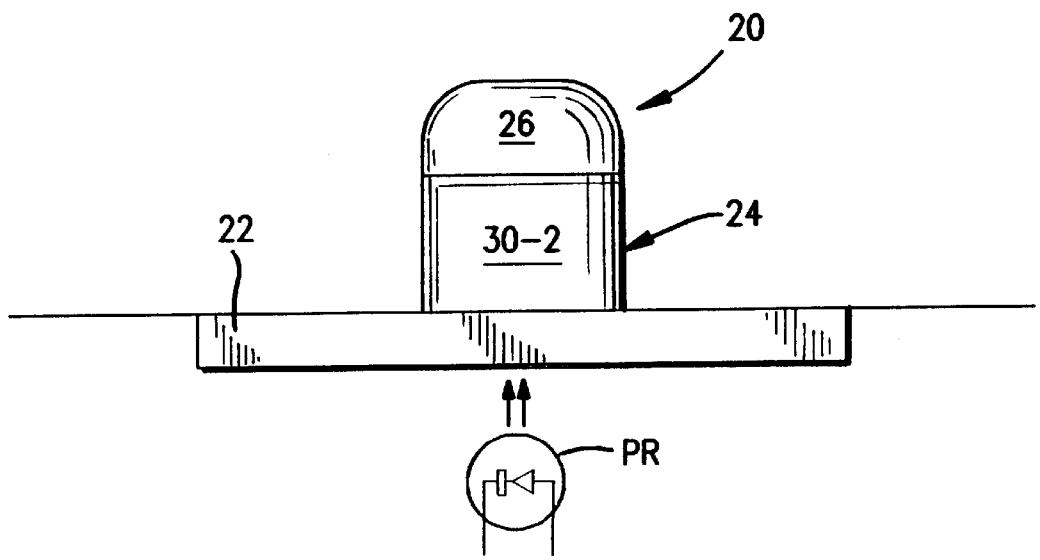
FIG. 10 is a side elevational view of the detector depicted in FIG. 7 as taken along line 10—10 therein.
Figure 11:
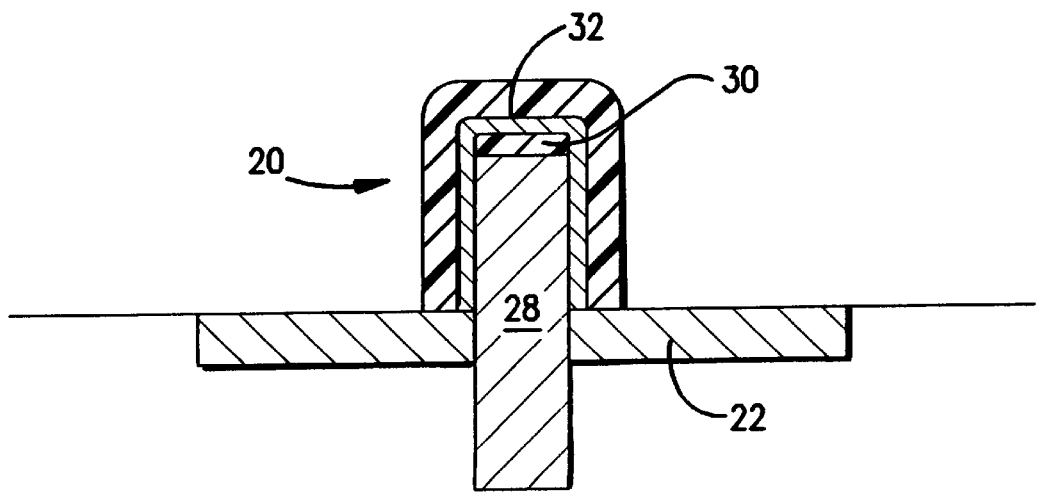
FIG. 11 is a longitudinal cross-sectional view of the detector depicted in FIG. 7 as taken along line 11—11 therein.

Accompanying FIG. 5 depicts a modification of the device 10 shown above which allows hinged articulation to occur between the sensing head 16 and the stem 14. In this regard, it will be observed that the distal end of the stem 14 includes a U-shaped yoke comprised of a pair of parallel, laterally spaced fingers 14-1, 14-2. The sensing head 16 includes a proximally projecting boss 16-8 which is sandwiched between the fingers 14-1 and 14-2 so as to be in interference fit therewith. Mechanical stability may be increased by providing a hinge pin (not shown) with its ends embedded in the fingers 14-1 and 14-2, and extending through the boss 16-8 to allow the sensing head 16 to pivot therearound (arrow A in FIG. 5). Also, the head 16 may be positioned between the yoke fingers 14-1, 14-2, in which case the proximally projecting boss 16-8 may be omitted. Furthermore, detents may be provided as desired to frictionally lock the sensing head in one of several angular orientations relative to the stem 14. In such a manner, the user may angularly adjust the orientation between the sensing head 16 and the stem 14 to ensure proper presentation of the detector 18 to the external cervical os.

Accompanying FIGS. 6–11 depict another embodiment of a refractive index detector 20 that may be employed instead of the detector 18 in the device 10 described above. In this regard, it will be observed that the detector 20 includes a stainless steel support plate 22 which may be embedded into the sensing head 16 of the device 10. Unlike the detector 18 discussed previously (which is substantially coplanar with the exterior surface of the sensing head 16), the detector 20 protrudes upwardly from the surface of the sensing head 16 and thus provides a pair of lateral active surfaces or "windows" in the light guide for detecting the refractive index of the cervical mucus.

The detector 20 includes generally a base section 24 having a generally triangular cross-section with a convexly protruding upper section 26 extending from its apex. The base section 24 includes a central stainless steel support member 28 having a triangularly shaped cross-section embedded within the fluorocarbon light guide 30. A U-shaped reflector 32 is positioned over the apex of the support member 28 so as to guide light therearound. The surfaces 28-1 and 28-2 are highly polished reflective surfaces corresponding to the active window surfaces 30-1 and 30-2 of the light guide 30.

The structures of the detector 20 shown in FIGS. 6–11 permit the light source LS (e.g., a light emitting diode) and photoreceptor PR (e.g., a photodiode) to be positioned below the base plate 22. Thus, the light source LS and photoreceptor PR can conveniently be encased completely by the biomedically compatible plastics material forming the sensing head 16. Furthermore, the convexly protruding upper section 26 provides a convenient tactile positioning aid to the user in locating the detector within the external cervical os. In such a manner, therefore, the active surfaces 30-1 and 30-2 of the light guide 30 may be brought into direct contact with the cervical mucus so that accurate refractive index readings may be obtained.

Figure 12:
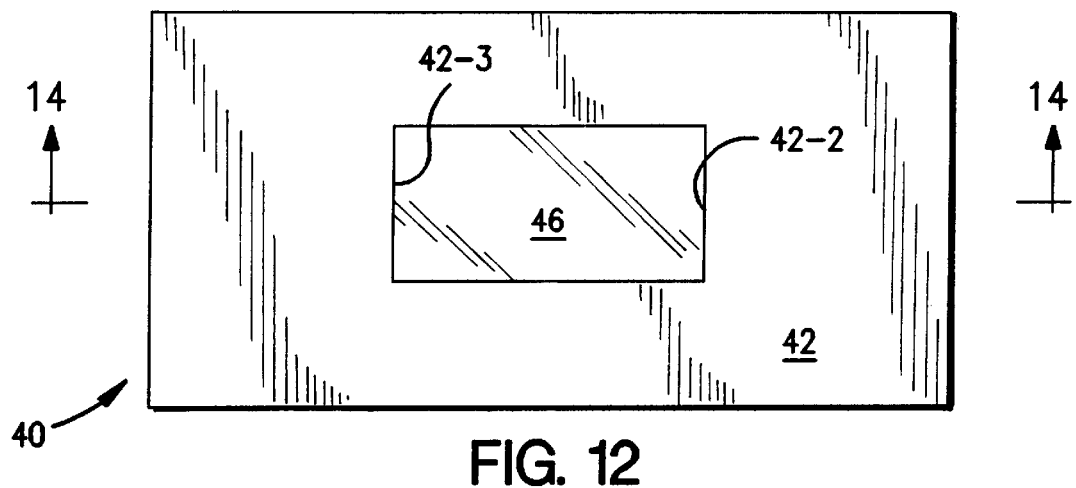
FIG. 12 is an enlarged top plan view showing a modified distal (sensing) end in accordance with another embodiment of this invention.
Figure 13:
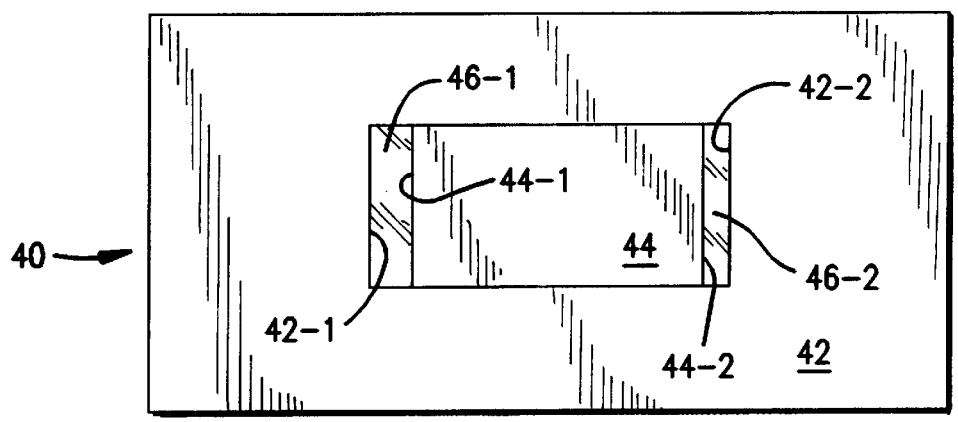
FIG. 13 is a bottom plan view of the embodiment depicted in FIG. 12.
Figure 14:
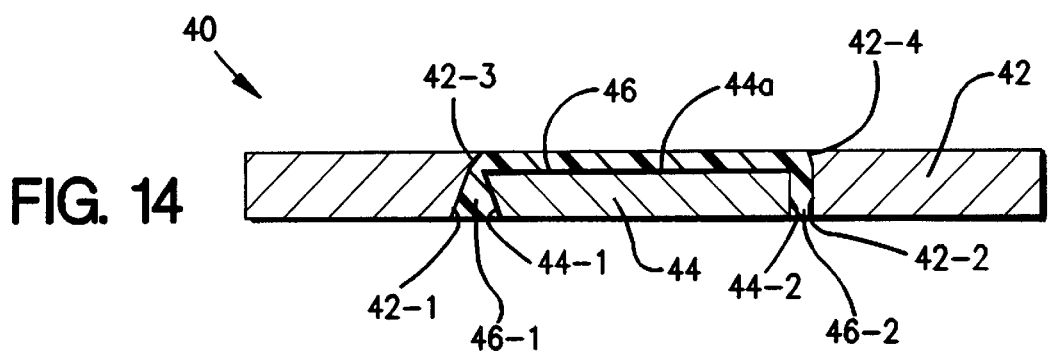
FIG. 14 is a cross-sectional elevational view through the detector section of the embodiment depicted in FIG. 12 as taken along line 14—14 therein.
Figure 18:
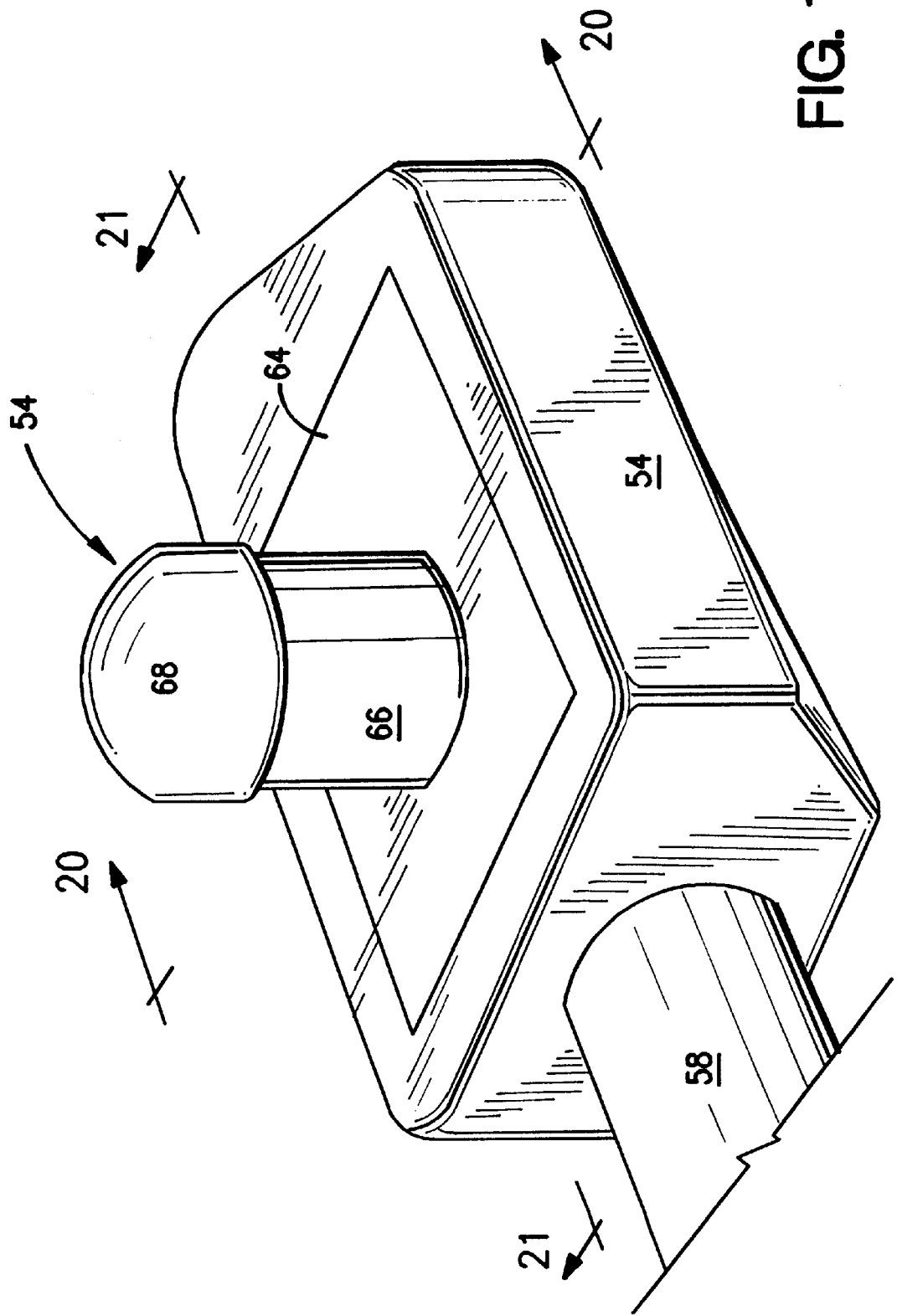
FIG. 18 is an enlarged perspective view of the distal (detector) end of the device shown in FIG. 15.
Figure 19:
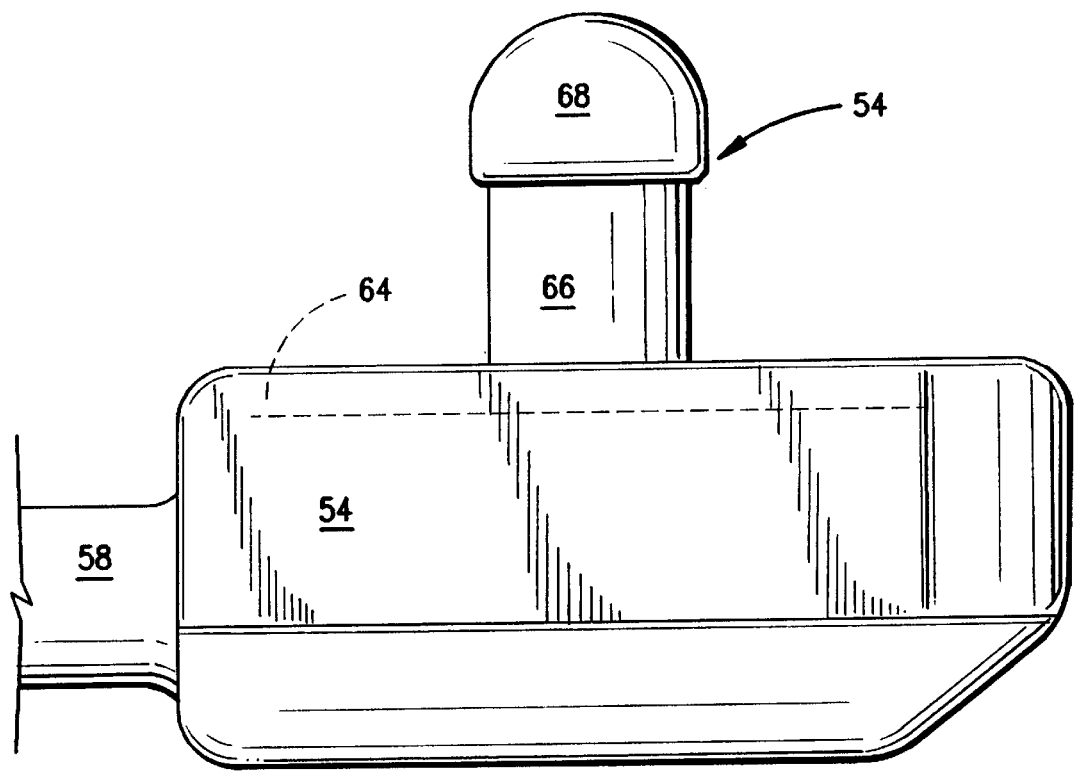
FIG. 19 is a side elevational view of the detector depicted in FIG. 18.

Another refractive index detector 40 that may be employed in the device 10 is depicted in accompanying FIGS. 12–14. As can be observed, the detector 40 is generally planar and comprised of a primary support plate 42 which defines a central window for receiving a secondary support plate 44, each of which is preferably formed of stainless steel. The secondary support plate 44 is configured so as to be relatively thinner in cross-sectional thickness as compared to the primary support plate 42. As such, the reflective surface 44a of the secondary support plate 42 is recessed from the upper surface of the primary support plate 42 so as to provide space for the fluorocarbon light guide 46.

The longitudinal edges 44-1, 44-2 and 42-1, 42-2 of the secondary and primary support plates 44, 42, respectively, define therebetween inlet and outlet spaces which are filled with a fluorocarbon polymer and thereby establish inlet and outlet light conduits 46-1 and 46-2, respectively, which are oriented in a plane that is substantially perpendicular to the active surface of the light conduit 46. In this regard, the inlet light conduit 46-1 is generally triangular in cross-section by virtue of the opposed beveled edges 42-1 and 44-1 of the primary and secondary support plates 42, 44, respectively. Furthermore, the longitudinally opposed edges 42-3 and 42-4 of the primary support plate 42 are beveled so as to help reflect light into and out of the planar light guide 46.

It will be further observed that the light guides associated with the detectors 18, 20 and 46 are each planar and have a substantially uniform thickness dimension along their lengths and widths. However, as will be discussed in greater detail below, the light guides may be convexly curvelinear. Such curvelinear light guides, however, will still have a substantially uniform thickness dimension along their lengths and widths similar to the planar light guides already discussed above.

The light guides of this invention will have an aspect ratio—that is t/l where t is the thickness of the light guide and l is the wetted length of the light guide—of between about 1:10 to about 1:20. The aspect ratios of the detectors of this invention thus translate into wetted lengths of between about 0.050 to about 0.300 inch, and more preferably between about 0.100 to about 0.200 inch. Thus, each of the active surfaces for paired active surface detectors according to this invention (e.g., the embodiment depicted in FIG. 6), will be one-half of the total wetted length dimension noted above.

Another embodiment of a device 50 according to the present invention is depicted in accompanying FIGS. 15–17. Like the device 10 described previously, the device 50 includes a proximal handle 52 and a distal sensing head 54. The handle 52 includes a battery pack 52-1, a processor 52-2, visual display 52-3 and operational button 52-4 which serve similar functions to those similar components described above with reference to FIG. 1.

The sensing head 54 carries a detector 56 (to be described in greater detail below). However, unlike the device 10 discussed previously (which employs an entirely rigid stem 14), the sensing head 54 is connected to the handle 52 by means of a longitudinally flexible, but torsionally rigid, stem 58. The longitudinal flexibility of the stem 58 thus allows the device 50 to be configured so as to accommodate individual anatomical differences in the orientation of the external cervical os and vagina. At the same time, the torsional rigidity of the stem 58 permits the user to rotate the sensing head 54 to permit tactile placement of the detector within the external cervical os so that precise refractive index readings may be obtained.

In use, a distal portion of the stem 58 is rotationally supported by a lateral support member 60 (see FIG. 17) which may be attached to a user's finger F by means of an adjustable elastic (or similar) band 62. As such, the sensing head 54 is positioned laterally parallel to the user's finger tip. The user may thus manipulate the handle with one hand and rotate the sensing head 54 so that the detector 56 is in contact with the finger tip on the other hand to which the device 50 is attached. The user may then manually locate their external cervical os and, once located, may rotate the sensing head 54 in an opposite direction so that the detector 56 is actually positioned therewithin. Once positioned within the external cervical os, the user may operate button 52-4 and thereby obtain a reading indicative of the refractive index of the cervical mucus (which thus correlates to the user's ovulation period).

Accompanying FIGS. 18–22 depict in greater detail the sensing head 54 and detector structures employed in device 50. In this regard, the sensing head 54 is most preferably formed of a biomedically compatible plastics material in which a stainless steel base plate 64 of the detector 54 is embedded. The detector 54 extends upwardly from the base plate 64 and includes a cylindrical sensing post section 66 and a convexly domed locator head section 68 most preferably unitarily formed from the same fluorocarbon polymer.

A central stainless steel support member 70 having a generally rectangular shaped cross-section is embedded within the fluorocarbon polymer forming the cylindrical post 66. In this regard, the opposed sides of the central support member 70 are convexly curved so as to correspond to the curvature of the post 66 and are polished to provide a reflective surface for the light traveling through the light guide regions 66-1 and 66-2 (see FIG. 21). A 90° angled reflector 72 having a pair of support arms 72-1, 72-2 and an angular cap 72-3 is provided so that the cap 72-3 is positioned over the top of the support member 70. Light being refracted along the light guide 66-1 will thus be redirected to the light guide 66-2 by virtue of the angular cap structure 72-3. The light guide regions 66-1 and 66-2 thus establish surfaces corresponding to the active window surfaces of the post 66. Placement of the detector 54 in a woman's external cervical os will therefore permit the cervical mucus to come into contact with the active surfaces of the light guides 66-1 and 66-2 so that refractive index measurements may be detected by comparing the amount of light which is refracted back to the photoreceptor PR to the amount of light emitted by the light source LS. It will be observed that, although convexly curved, the light guides 66-1 and 66-2 have a substantially constant thickness dimension.

Further understanding of this invention will be obtained from the following non-limiting Example.

EXAMPLES

I. Example I

A 2×2 inch square of sample material was cut from a sheet of 1000L FEP Teflon® film (0.010 inches thick) manufactured by DuPont High Performance Films, which reportedly was made from NP-40 FEP resin of Daikin Industries, Ltd. The sample was heat-treated using a laboratory heat-treatment/quenching press. The press had a pair of heated platens for melting a sample and a pair of freezing platens for rapidly quenching the sample. The tested sample was heated for 45 seconds between the hot platens at 657° F., then quenched between the quench platens immersed in liquid nitrogen (minus 320° F.). A transfer arm enabled the hot mold containing the sample to be swung rapidly between the heated and the quench platens.

Each pair of platens included a stationary platen and a platen that was attached to the piston rod of an air cylinder to allow the platens to be opened and closed rapidly. The air cylinders also provided a force that kept the mold flat and in intimate contact with the platens.

The sample itself was contained within a mold comprised of a silver/stainless steel/silver sandwich structure. Initially the sandwich is loosely held together by small screws at the periphery, but the force of the platens and the adhesion of the molten sample keep the sandwich together during processing. The top layer of the sandwich was a polished sheet of 99.9% silver (Fine Silver) having a thickness of 26 gage (0.016 inches) before polishing and had a rectangular geometry, 3 inches by 3.5 inches which was lapped flat and polished on both sides. One side of the silver contacted the platen; while the other side acted as the top surface of the mold for the sample. The side facing the sample must be polished to ensure that the sample will have a smooth surface after melting and quenching. The reverse side was polished to give good contact with the platen for high heat transfer capability. The middle layer of the sandwich was 0.010 inch thick shim stock (stainless steel alloy AISI 302) having a 2-inch square hole which formed the sides of the mold. The thickness of the shim stock establishes the final thickness of the sample. The shim stock extends laterally from the sandwich and was attached rigidly to the transfer arm. The bottom layer of the sandwich was another sheet of Fine Silver. It is similar to the above described top sheet except that it formed the bottom of the mold.

The hot platens were made of aluminum (alloy 6061). For each platen, the surface that contacted the mold sandwich was a 3-inch square which was lapped and polished for good heat transfer capability. Each hot platen had (2) 200 watt cartridge heaters and were controlled in parallel by a rheostat control so that temperature could be adjusted for optimum conditions. Temperature was measured with a surface contact thermometer. There was also provision for leveling the lower platen so that the platen surfaces are parallel when the mold sandwich is squeezed between them.

The cold platens were made of copper (alloy 110, 99.9% pure) so as to provide sufficient heat transfer during quenching. It is important that there is sufficient mass of copper to absorb the quantity of heat from the sample and sample mold to achieve quenching. The required heat capacity is governed by the mass of the pieces and the following thermal processes: heat of solidification of the sample, cooling of the sample, cooling of the silver plates and cooling of the stainless steel shim stock. For the apparatus described here, there was a minimum of 1 inch copper behind the polished surface of each platen. For each platen, the surface that contacted the mold sandwich was a 3-inch square which was lapped and polished for high heat transfer capability. The bottom platen resides in a stainless steel pan.

Before the melting/quenching process began, the bottom platen was partially immersed in liquid nitrogen with only the top surface protruding by approximately 0.25 inches until the nitrogen boiling is minimal. The top platen was machined with a 1 inch deep well in its top surface. Before the melting/quenching process began, this well was filled with liquid nitrogen until the nitrogen boiling is minimal. The time dependent cooling of the platens was characterized using a themocouple embedded in a Teflon® fluoropolymer sheet squeezed between the platens. Whenever the nitrogen boiling became minimal, the measured temperature was below −315° F. The quench platens and stainless steel pan of liquid nitrogen were surrounded by a double layer box of 0.775 inch Styrofoam® (1.55 inches total). Fifteen seconds before sample transfer, a "window" of Styrofoam® insulator material was removed to allow the transfer arm to swing between the quenching platens. There was also provision for leveling the lower platen so that the platen surfaces are parallel when the mold sandwich is squeezed between them.

A sample heat treated in the above-described manner and an untreated sample were tested per ASTM D 1003-61 (reapproved 1988). As allowed by ASTM D1003-61, each sample was immersed in isopropyl alcohol prior to testing so as to negate the effects of surface flaws. The untreated sample had a haze value of 2.6% (corresponding to an optical clarity of 97.4%) which is inadequate for use in the present invention while the heat treated sample had a haze value of 1.0% (corresponding to an optical clarity of 99.0%) and is satisfactory for use in the present invention.

Example II

A device employing a detector similar to that depicted in FIGS. 1–4 was constructed in order to investigate refractometric measurements using sucrose solutions. The detector comprised a transparent light conduit made of fluorinated ethylene propylene (FEP) positioned between a light emitting diode (LED) and a photodiode detector.

The light conduit portion of the detector was a portion of a Teflon® FEP fluorocarbon film (DuPont) measuring 0.010" thick×0.200" long×0.200" wide. The clarity of the film had been increased by heating it above its glass transition temperature followed by a rapid quench into an aqueous solution of calcium chloride at approximately −49° C. The film was sandwiched between polished stainless steel sheets during heating and quenching to give two smooth faces, top and bottom, upon removal from the sheets. The bottom face of the film was then glued to two stainless steel supports separated by parallel channel 0.060" wide. The film was unsupported along the channel at its bottom surface thereby allowing air contact for the length of the film.

A red LED (Panasonic LN21CVAL(URS)) and a photodiode (Jameco Company P/N 112168) each of T 1¾ style were modified by cutting off their convex lenses and polishing them flat close to the anode wire and parallel to the embedded chip. The components were arranged such that the axis of the LED, axis of the FEP film light conduit and axis of the photodiode all coincided to allow the maximum light transmission through the FEP conduit to the photodiode. The components were epoxied in place. Black paint was used to mask all light paths from the LED to the photodiode except for paths through the 0.060"×0.010"×0.200" conduit of the FEP film.

The LED was wired in series with a 328 ohm resistor, and during testing, a regulated 9.00 volts was applied across the pair. Similarly, the photodiode was wired in series with a 993 ohm resistor, and during testing, a regulated 9.00 volts was applied across the pair. The voltage across the LED/resistor pair remained constant, and the measured voltage across the resistor (7.23 volts) indicated a current flow of 22.0 milli-amperes through the series combination. The voltage across the photodiode varied in response to the refractive index of the medium against the top face of the FEP film. This voltage was measured by use of a multimeter (Fluke 8021 B). A separate multimeter (Fluke 73 Series II) was used to verify that the source voltage did not vary. Both meters agreed with each other within one digit of resolution (0.01 volts) over the range of measurement. Initial drift of the voltage source (BK Precision model #1651) by 0.04 volt was eliminated by a two hour warm-up of the instrument. No variation of the instrument was measured during testing.

Test solutions were made by mixing sucrose (EM Science P/N SX1075-1) with reverse osmosis deionized (RODI) water whose purity exceeds 15 Megohm-cm. The sucrose was dried in an oven at 105° C. for several hours, followed by storage overnight under vacuum at about 40 milli-torr. Solutions were mixed in 10 gram amounts on a weight/weight basis with milligram accuracy (Mettler model #AT200) into 15 milli-liter centrifuge tubes (Corning P/N 25310-15) and capped. The following solutions were made: 0% (unaltered RODI), 1, 2, 4, 6, 8 and 10%. Refractive index was measured for each solution to five decimal places at 25° C. (Bellingham and Stanley model #RFM 340). The solutions were measured before and after testing of the detector. Measurements with the RFM 340 were repeatable to within n=0.00014.

Characterization of the detector was made in a room whose temperature was controlled between 25.0°–25.4° C. 100 microliters of a particular solution was placed on the FEP film and immediately covered with a large, opaque cup to exclude ambient light. Readings were made within 30 seconds, and there was no measured change of the reading after covering. After each sample, the FEP film surface was rinsed with RODI water and dried with a tissue. The samples were measured in the following order: 2, 6, 1, 10, 4, 8, 0% (set #1). After one hour, in which the power supply was left on, the samples were measured in the following order: 0, 1, 2, 4, 6, 8, 10% (set #2); then immediately followed by: 2, 6, 1, 10, 4, 8, 0% (set #3). Results are plotted in the graph of FIG. 23.

Figure 23:
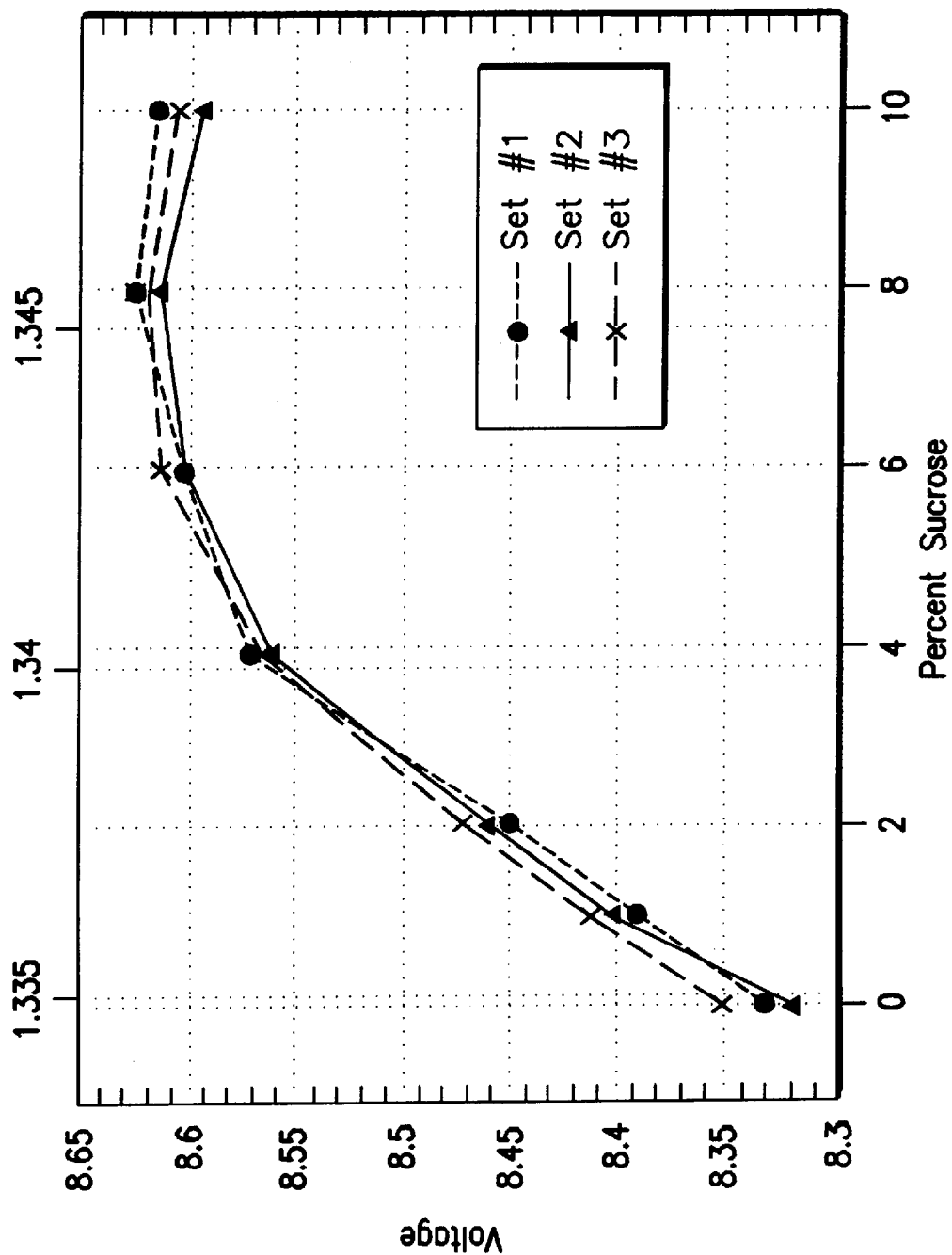
FIG. 23 is a graph of the voltage across a photodiode versus concentration and refractive index of sucrose solutions obtained from the data of the Example below.

The graphs of FIG. 23 shows some variation which may be due to residual fluid from previous samples or condensate on the underside of the conduit. The graphs all show a limiting value above refractive index n=1.34. These graphs demonstrate that high resolution over a relatively narrow range of sucrose solutions may be obtained with the detector of this invention.

The devices of this invention have been discussed in terms of their presently preferred embodiment, namely, as a means to detect in vivo hydration of cervical mucus. However, other end use applications may be identified by those skilled in this art. Suffice it to say, however, that the refractive index of the fluorocarbon polymer employed as the light guide must be matched to the refractive index range that is desired to be measured.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A device for the in vivo detection of refractive indices of cervical mucus at a female's cervical os which comprises a distal sensing head for intravaginal placement against the female's cervical os; and a refractive index detector carried by said distal sensing head and having (i) a light source, (ii) a photoreceptor which receives light from said light source and outputs a signal indicative of the refractive index of the cervical mucus, and (iii) a light guide positioned so as to guide light from the light source to the photoreceptor, said light guide having at least one active surface to be wetted by the cervical mucus which consists essentially of a fluorocarbon polymer having an optical clarity of greater than about 98% and a refractive index of between about 1.335 to about 1.450.

2. The device of claim 1, wherein the light guide has an aspect ratio of between about 10:1 to about 20:1.

3. The device of any one of claim 1 or 2, wherein the fluorocarbon polymer is selected from copolymers comprised of tetrafluoroethylene with hexafluoropropylene comonomers, polychlorotrifluoroethylene, ethylene-tetrafluoroethylene copolymers, polyvinylidene fluoride polymers, and polyvinyl fluoride polymers.

4. The device of claim 1, having a proximal handle, and a stem connecting said handle to said sensing head.

5. The device of claim 4, wherein said stem is longitudinally rigid.

6. The device of claim 4, wherein said stem is longitudinally flexible.

7. The device of claim 6, wherein said stem is torsionally rigid.

8. The device of claim 4, wherein said handle includes an electrical power source and a visual display indicative of detected refractive index.

9. The device of claim 4, wherein said sensing head is pivotally connected to said stem to allow for angular adjustments therebetween.

10. The device of claim 1, wherein said detector includes a central support rod having a polished light-reflective surface, and wherein said light guide includes said fluorocarbon polymer supported by said support rod.

11. The device of claim 10, wherein said light guide is positioned axially between said light source and said photoreceptor.

12. The device of claim 1, wherein said detector is substantially planar.

13. The device of claim 1, wherein said detector is curvelinear.

14. A device for the in vivo detection of the refractive index of cervical mucus, said device comprising:

a proximal handle to allow vaginally external manual manipulation of the device;

an elongate stem projecting from said handle and being sufficiently slender for vaginal penetration; and a distal sensing head connected to a distal end of said elongate stem and having a planar sensing surface which is angularly oriented with respect to said elongate stem for in vivo intravaginal placement adjacent to the external cervical os; wherein said sensing head includes a planar refractometer for obtaining a measurement of the cervical mucus refractive index at the external cervical os, said refractometer including;

(i) a light source for emitting light;

(ii) a photoreceptor which receives a portion of the light emitted by the light source and issues a signal indicative of the refractive index of the cervical mucus;

(iii) a light guide which guides light between said light source and said photoreceptor and which consists essentially of a fluorocarbon polymer having an optical clarity of greater than about 98% and a refractive index of between about 1.335 to about 1.450, wherein (iv) said light guide has at least one active window which is coplanar with said planar sensing surface of said distal sensing head for contact with the cervical mucus when said sensor surface is placed against the cervical os to allow absorption of at least some of the light emitted by the light source so that said photoreceptor detects remaining unabsorbed light and issues a signal in response thereto;

(iv) a processor which receives said signal from said photoreceptor and determines the refractive index of said cervical mucus therefrom.

15. The device of claim 14, wherein the light guide has an aspect ratio of between about 10:1 to about 20:1.

16. The device of claim 14 or 15, wherein the fluorocarbon polymer is selected from copolymers comprised of tetrafluoroethylene with hexafluoropropylene comonomers, polychlorotrifluoroethylene, ethylene-tetrafluoroethylene copolymers, polyvinylidene fluoride polymers, and polyvinyl fluoride polymers.

17. The device of claim 14, wherein said stem is longitudinally rigid.

18. The device of claim 14, wherein said stem is longitudinally flexible.

19. The device of claim 18, wherein said stem is torsionally rigid.

20. The device of claim 14, wherein said handle includes an electrical power source, and wherein said processor includes a visual display indicative of the refractive index of the cervical mucus.

21. The device of claim 14, wherein said sensing head is pivotally connected to said stem to allow for angular adjustments therebetween.

22. The device of claim 14, wherein said light guide is positioned axially between said light source and said photoreceptor.

23. The device of claim 14, wherein said light source and said photoreceptor are oriented coaxially with said light guide.

24. The device of claim 14, wherein said light source and said photoreceptor are located below said light guide, and wherein said light guide includes a light inlet and a light outlet adjacent said light source and said photoreceptor, respectively, which are oriented at substantially right angles to said light guide.

25. The device of claim 24, wherein said light inlet has a greater widthwise dimension as compared to said photoreceptor.

26. A refractometer for determining refractive indices of liquid comprising:

a light source, a photoreceptor which receives light from said light source and outputs a signal indicative of the refractive index of the liquid;

a light guide positioned so as to guide light from the light source to the photoreceptor, said light guide having at least one active surface to be wetted by the liquid, wherein said light guide consists essentially of a fluorocarbon polymer having an optical clarity of greater than about 98% and a refractive index of between about 1.335 to about 1.450.

27. The detector of claim 26, wherein the light guide has an aspect ratio of between about 10:1 to about 20:1.

28. The detector of any one of claim 26 or 27, wherein the fluorocarbon polymer is selected from copolymers comprised of tetrafluoroethylene with hexafluoropropylene comonomers, polychlorotrifluoroethylene, ethylene-tetrafluoroethylene copolymers, polyvinylidene fluoride polymers, and polyvinyl fluoride polymers.

29. The detector of claim 26, wherein said at least one active surface is planar.

30. The detector of claim 26, wherein said at least one active surface is curvelinear.

31. A planar refractometer comprising:
  (i) a light source;
  (ii) a photoreceptor axially spaced from said light source to receive transmitted light therefrom and output a signal indicative of refractive index of a sample fluid;
  (iii) a cross-sectionally U-shaped, rigid polished support channel extending between said axially spaced apart light source and photoreceptor;
  (iv) a light guide positioned within said support channel, wherein
  (v) upper surfaces of said support channel and said light guide are substantially coplanar with one another, and wherein
  (vi) said light guide consists essentially of a fluorocarbon polymer having an optical clarity of greater than about 98% and a refractive index of between about 1.335 to about 1.450.

32. The refractometer of claim 31, wherein said support channel is defined by a bottom polished metal support rod and an opposed pair of lateral polished metal support rods.

33. The refractometer of claim 31, wherein said upper surfaces of said light source, photoreceptor and said support channel are each covered with an opaque material to thereby leave an uncovered active window of said light guide.

34. The refractometer of claim 31, wherein the light guide has an aspect ratio of between about 10:1 to about 20:1.

35. The refractometer of claim 31, wherein the fluorocarbon polymer is selected from copolymers comprised of tetrafluoroethylene with hexafluoropropylene comonomers, polychlorotrifluoroethylene, ethylene-tetrafluoroethylene copolymers, polyvinylidene fluoride polymers, and polyvinyl fluoride polymers.

36. A device for the in vivo detection of cervical mucus refractive index comprising a handle, a stem extending from said handle, and a distal sensing head which includes a refractometer as in any one of claims 27–35.

* * * * *